US006989346B2

(12) United States Patent
Heineke et al.

(10) Patent No.: US 6,989,346 B2
(45) Date of Patent: Jan. 24, 2006

(54) PREPARATION OF OLEFINS, PARTICULARLY OF PROPYLENE, BY DEHYDROGENATION

(75) Inventors: Daniel Heineke, Ludwigshafen (DE); Michael Baier, Mannheim (DE); Dirk Demuth, Mannheim (DE); Klaus Harth, Altleiningen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 121 days.

(21) Appl. No.: 10/340,282

(22) Filed: Jan. 13, 2003

(65) Prior Publication Data

US 2003/0163012 A1 Aug. 28, 2003

Related U.S. Application Data

(62) Division of application No. 09/331,052, filed as application No. PCT/EP97/06858 on Dec. 9, 1997, now Pat. No. 6,576,804.

(30) Foreign Application Priority Data

Dec. 27, 1996 (DE) ........................................ 196 54 391

(51) Int. Cl.
  *B01J 23/00* (2006.01)
  *B01J 23/40* (2006.01)
  *B01J 23/42* (2006.01)
  *B01J 23/58* (2006.01)
  *B01J 23/60* (2006.01)

(52) U.S. Cl. ....................... 502/308; 502/305; 502/306; 502/307; 502/313; 502/314; 502/317; 502/319; 502/325; 502/326; 502/327; 502/328; 502/329; 502/330; 502/332; 502/333; 502/334; 502/336; 502/337; 502/338; 502/339; 502/349

(58) Field of Classification Search ......... 502/305–308, 502/313–317, 319, 321, 325–330, 332–339, 502/349, 351
See application file for complete search history.

(56) References Cited

U.S. PATENT DOCUMENTS

| | | | |
|---|---|---|---|
| 2,375,021 A | 5/1945 | Morrell ...................... | 585/629 |
| 4,131,628 A * | 12/1978 | Antos et al. ................. | 585/434 |
| 4,677,237 A | 6/1987 | Imai et al. ................... | 585/444 |
| 4,891,343 A | 1/1990 | Quadair ...................... | 501/103 |
| 4,977,114 A * | 12/1990 | Horinouchi et al. ........ | 501/104 |
| 5,002,917 A | 3/1991 | Deller et al. ................ | 502/242 |
| 5,075,277 A | 12/1991 | Saiai et al. .................. | 502/333 |
| 5,089,455 A | 2/1992 | Ketcham et al. ............ | 501/104 |
| 5,206,192 A | 4/1993 | Dransfield et al. .......... | 501/103 |
| 5,243,122 A | 9/1993 | Brinkmeyer et al. ........ | 585/654 |
| 5,254,787 A | 10/1993 | Dessau ....................... | 585/654 |
| 5,401,893 A | 3/1995 | Gosling et al. ............. | 585/322 |
| 5,447,898 A | 9/1995 | Blankenstein et al. ...... | 502/349 |
| 5,510,553 A | 4/1996 | Delorme et al. ............ | 585/444 |
| 5,510,557 A | 4/1996 | Gartside et al. ............ | 585/654 |
| 5,556,816 A | 9/1996 | Kim et al. ................... | 501/103 |
| 5,600,046 A | 2/1997 | Gosling et al. ............. | 585/322 |
| 5,658,837 A | 8/1997 | Quadir ....................... | 501/103 |
| 5,779,784 A | 7/1998 | Eadon et al. ............... | 106/450 |
| 5,786,294 A | 7/1998 | Sachtler et al. ............. | 502/349 |
| 5,877,369 A | 3/1999 | Wu et al. .................... | 585/419 |
| 5,977,013 A * | 11/1999 | Elliott et al. ................ | 502/337 |
| 6,034,029 A | 3/2000 | Wulff-Doring et al. ..... | 502/308 |
| 6,037,303 A | 3/2000 | Peratello et al. ............ | 502/217 |
| 6,049,007 A | 4/2000 | Riechers et al. ............ | 564/302 |
| 6,140,545 A | 10/2000 | Merger et al. .............. | 568/799 |

FOREIGN PATENT DOCUMENTS

| | | |
|---|---|---|
| EP | 403 462 | 12/1990 |
| WO | WO 95/23123 | 8/1995 |

OTHER PUBLICATIONS

Wan et al. "Conversion of Propane in HZSM–5 and in Transition Metal HZSM–5" Jnl of Chin. I. Ch. E., vol. 21, No. 3, (1990) pp. 167–172.

Vora et al. "Oleflex: $C_2$—$C_5$ Dehydorgenation Updated" Energy Progress vol. 6, No. 3, (1986) pp. 171–175.

Husted et al, "Catalytic Dehydrogenation for the Production of LPG Olefins and Derivatives" Chemica 83 (1983) pp. 663–672.

Xianzhi et al. "Study on the N–High Efficiency Catalyst for Propylene Polymerization" pp. 511–515.

Delmon "Catalyst Deactivation 1994" vol. 88 (1994) pp. 519–524.

* cited by examiner

*Primary Examiner*—Cam N. Nguyen
(74) *Attorney, Agent, or Firm*—Novak Druce & Quigg, LLP

(57) ABSTRACT

Olefinically unsaturated hydrocarbons are prepared from corresponding paraffinic hydrocarbons, in particular propylene is prepared from propane, by dehydrogenation over a catalyst comprising an oxide of a transition metal of group IV B of the Periodic Table, eg. $TiO_2$ or $ZrO_2$, and possibly at least one element selected from among elements of transition group VIII, eg. palladium, platinum or rhodium, and/or an element of transition group VI, eg. chromium, molybdenum or tungsten, and/or rhenium and/or tin and possibly a compound of an alkali metal or alkaline earth metal, a compound of main group III or transition group III or zinc.

4 Claims, No Drawings

PREPARATION OF OLEFINS, PARTICULARLY OF PROPYLENE, BY DEHYDROGENATION

This application is a divisional application of Ser. No. 09/331,052, filed Jun. 16, 1999, now U.S. Pat. No. 6,576,804, which is a National Stage filing of Appl. No. PCT/EP97/06858, filed Dec. 9, 1997.

BACKGROUND OF THE INVENTION

At present, propylene is mostly isolated from the product mixture formed in the steam cracking of light naphtha. Economic and other reasons make it desirable to have a more flexible raw material basis. An alternative to isolation of propylene from mixtures in which it is present is the dehydrogenation of propane.

As a non-oxidative route, propylene can be obtained by dehydrogenation of propane over noble metal catalysts such as $Pt/Al_2O_3$, $Pt/Sn/Al_2O_3$ or over noble metal-free catalysts such as $Cr/Al_2O_3$. The reaction is strongly endothermic and proceeds at a satisfactory rate only at a high temperature. This promotes secondary reactions, eg. degradation of the propane to form ethylene and methane; at the same time, ethylene is hydrogenated by the hydrogen liberated in the dehydrogenation. The selectivity of the reaction decreases greatly with increasing conversion because of the by-product-dependent competing reactions, which makes the industrial implementability of the process questionable. In addition, secondary reactions lead to carbon deposits on the catalysts used, which would have to be regenerated after relatively short periods of operation.

In a process which has achieved industrial maturity, the dehydrogenation is carried out at low pressure and relatively high temperature and the catalyst is continuously regenerated using atmospheric oxygen (Energy Prog. (1986), 6(3) 171–6 and Chem. Eng. Today, Copying Uncertainty, Aust. Chem. Eng. Conf. 11th (1983), 663–71). The process can be carried out using $Pt/Al_2O_3$ catalysts in a moving bed at 600–700° C. and a pressure of 2–5 bar.

The process described in WO 9523123 uses $Cr/Al_2O_3$ catalysts which are operated cyclically, ie. using a regenerative procedure. In this process, the propane is preheated using the waste heat liberated in the burning-off of the carbon. $Pt/Sn/Al_2O_3$ catalysts are known from Shiyou Huagong (1992), 21(8), 511–515. That reference also discloses that these catalysts can be doped with potassium or magnesium. Doping with tin is said to slow the deactivation, despite formation of carbon deposits (Stud. Surf. Sci. Catal. 1994, 88, 519–24).

Oxidic catalysts comprising redox-active elements which are not present in their lowest oxidation state are described in EP-A-403 462.

The dehydrogenation of propane using zeolites of the ZSM-5 type is likewise known. If these zeolites are doped with zinc, this influences the acid-base behavior of the zeolites: cracking reactions are said to be largely suppressed (J. Chin. Inst. Chem. Eng. (1990), 21(3), 167–72).

The processes which have become known have, in particular, the disadvantage that the selectivity decreases greatly with increasing conversion. In addition, the catalysts have to be regenerated frequently, which is extremely disadvantageous for an industrial process.

OBJECT OF THE INVENTION

It is an object of the present invention to remedy the above-mentioned disadvantages and to provide catalysts which make possible a process for preparing, in particular, propylene and other low molecular weight olefins by dehydrogenation of corresponding paraffinic hydrocarbons and which achieve a high selectivity even at a high conversion.

DETAILED DESCRIPTION OF THE INVENTION

We have found that this object is achieved by the use of catalysts based on ceramic oxides of transition group IV of the Periodic Table of the Elements, preferably having more than 90% in one crystalline modification, which can comprise a dehydrogenation-active element and possibly further elements.

Suitable ceramic oxides are, in particular, zirconium oxide ($ZrO_2$) and titanium oxide ($TiO_2$). The ceramic oxide can be doped with from 0.005 to 5% by weight of a metal of transition groups VI and VIII such as palladium, platinum and/or rhodium. Suitable dehydrogenation-active elements are especially metals of transition group VIII, with the noble metals platinum and palladium being particular suitable; preference is given to platinum.

If a noble metal is used as dehydrogenation-active element, it is possible to make additional use of from 0.005 to 5% by weight of metals which can slow the sintering of the noble metal, for example rhenium, Ir and Sn, in particular Re and Sn.

Possible further elements are those which are known to be able to influence the acidity of the catalyst surface or to stabilize noble metals against sintering. Such further elements are all elements of main groups I and II, ie. Li, Na, K, Rb, Cs on the one hand and Mg, Ca, Sr and Ba on the other hand. Suitable elements of main group III are, in particular, gallium, indium and thallium. Suitable elements of transition group III are, in particular, Y and La and also rare earth elements. Zinc has also been found to be effective.

The use of the ceramic oxides of transition group IV is essential for the purposes of the present invention, while the other constituents are only of importance for the base reaction and play a supporting role. Thus, other dehydrogenation-active metals, for example from transition group VI, in particular chromium or molybdenum, can be present in place of a noble metal.

It is essential for the present invention that the crystalline phase of the zirconium oxide is stable under the conditions of the dehydrogenation. If tetragonal $ZrO_2$ is employed, this can be stabilized by doping with La or Y.

The pore width of the catalysts is preferably from 2 to 60 nm, where 10% of the pores have a width of more than 20 nm and the specific pore volume is from 0.1 to 1 ml/g.

Compared with the known catalysts, the catalysts of the present invention have the advantage of higher selectivity with simultaneously higher conversion in the dehydrogenation of propane to propylene. In addition, a further advantage found is that the catalysts of the present invention can be operated without additional hydrogen which would otherwise have to be used for suppressing the formation of carbon deposits. Further advantages are their high mechanical strength, high operating lives and easy shaping.

To prepare the catalysts of the present invention, it is possible to use amphoteric oxides of zirconium and titanium or their mixtures or suitable precursors which can be converted into the oxides by calcination.

The preparation process can be selected from among known model processes, for example the sol-gel process, precipitation of the salts, dehydration of the corresponding acids, dry mixing, slurrying or spray drying.

The doping with a basic compound can be carried out either during the preparation, for example by coprecipitation or subsequently by impregnation of the ceramic amphoteric oxide with a compound of the relevant alkali metal or alkaline earth metal compound, etc.

The dehydrogenation-active constituent is generally applied by impregnation with a suitable compound of the element concerned. Such a compound is selected so as to be able to be converted into the corresponding metal oxide by calcination. However, instead of impregnation, the dehydrogenation-active component can also be applied by other methods such as spraying. Suitable metal salts are, for example, the nitrates, acetates and chlorides of the corresponding metals; also possible are complex anions of the metals used. Preference is given to using $H_2PtCl_6$ or $Pt(NO_3)_2$ for platinum and $Cr(NO_3)_3$ or $(NH_4)_2CrO_4$ for chromium. Suitable precursors when using noble metals as dehydrogenation-active components also include the corresponding noble metal sols which can be prepared by one of the known methods, for example by reduction of a metal salt with a reducing agent in the presence of a stabilizer such as PVP. The preparation is described in detail in DE 195 00 366.

The catalyst can be used in a fixed bed or, for example, in the form of a fluidized bed and have an appropriate shape. Suitable shapes are, for example, granules, pellets, monoliths, spheres or extrudates having an appropriate cross-section, eg. wagon wheel, star, ring.

The content of alkali metal, alkaline earth metal or a metal of main group III or transition group III or a rare earth metal or zinc is up to 20% by weight, preferably from 1 to 15% by weight, particularly preferably from 1 to 10% by weight. Alkali metal and alkaline earth metal precursors used are advantageously compounds which can be converted directly into the corresponding oxides by calcination. Suitable examples are hydroxide, carbonate, oxalate, acetate or mixed hydroxycarbonates.

If the ceramic support is additionally or exclusively doped with a metal of main group III or transition group III, starting compounds in this case too should be ones which can be converted into the corresponding oxides by calcination. If lanthanum is used, examples of suitable compounds are lanthanum oxide carbonate, $La(OH)_3$ $La_3(CO_3)_2$, $La(NO_3)_3$ or lanthanum compounds containing organic anions, eg. lanthanum acetate, lanthanum formate or lanthanum oxalate.

The content of a dehydrogenation-active component in the catalysts is up to 10% by weight. It is also possible to use catalysts which contain no dehydrogenation-active element. If the catalyst is doped with a dehydrogenation-active element of transition group VIII as dehydrogenation-active element, the content is from 0 to 10% by weight, preferably from 0.2 to 8% by weight, particularly preferably from 0.5 to 2% by weight. If the catalyst is doped with a noble metal as dehydrogenation-active component, the content is from 0 to 5% by weight, preferably from 0.2 to 2% by weight, particularly preferably from 0.5 to 1.5% by weight.

The catalysts have a BET surface area of up to 500 $m^2/g$ or more, preferably 10–300 $m^2/g$, particularly preferably 20–100 $m^2/g$. The pore volume is generally from 0.1 to 1 ml/g, preferably from 0.15 to 0.6 ml/g, particularly preferably from 0.2 to 0.4 ml/g. The mean pore diameter, which can be determined by Hg penetration analysis, is from 0.008 to 0.06 µm, preferably from 0.01 to 0.04 µm.

The dehydrogenation of propane is carried out at 300–800° C., preferably 450–700° C., and at pressures at from 10 mbar to 100 bar, preferably from 100 mbar to 40 bar, at a WHSV (weight hourly space velocity; in [(g of starting material)·(g of cat.)$^{-1}$·h$^{-1}$] of 0.01 to 100, preferably from 0.1 to 20. Besides the hydrocarbon to be dehydrogenated, diluents such as $CO_2$, $N_2$, noble gases or steam may be present. If appropriate, ie. under severe reaction conditions, hydrogen can be added to the hydrocarbon stream; the ratio of hydrogen to hydrocarbon stream can be from 0.1 to 100, preferably 1–20. The added hydrogen serves to remove carbon deposits formed on the surface of the catalyst.

Apart from the continuous addition of a gas which prevents carbon deposits during the reaction, it is possible to regenerate the catalyst by passing hydrogen or air over it from time to time. The regeneration itself takes place at 300–900° C., preferably 400–800° C., using a free oxidizing agent, preferably using air, or in a reductive atmosphere, preferably using hydrogen. The regeneration can be carried out at subatmospheric, atmospheric or superatmospheric pressure. Preference is given to pressures in the range from 500 mbar to 100 bar.

EXAMPLES

Catalyst Preparation:

Examples 1–4

A 4 M $NH_3$ solution was added by stirring to a solution of 24.85 g of $ZrOCl_2·H_2O$ and 1.33 g of $La(NO_3)_3·6H_2O$ in 50 ml of water until no more precipitate formation was observed. The precipitate was filtered off, washed with water until free of chloride and dried for 16 hours at 120° C. The dried precipitate was suspended in 50 ml of a 0.02 M $(NH_4)_2CrO_4$ solution and the supernatant solution was evaporated at 50° C. The residue was dried for 16 hours at 120° C. and calcined for 4 hours at 600° C. The finished catalyst contained 0.66% of chromium and 5.3% of lanthanum. The crystalline phase of the zirconium dioxide was found to be predominantly tetragonal by X-ray analysis. The primary particle size of the zirconium dioxide was determined as about 5 nm by means of TEM.

In Example 1, the fresh catalyst was used. For Example 2, the same catalyst was used after regeneration at 500° C. using atmospheric oxygen. The catalyst regenerated for the second time using atmospheric oxygen was used for Example 3 and the catalyst regenerated for the third time was used for Example 4.

Examples 5 and 6

A catalyst was prepared by impregnation of $ZrO_2$ (support SN 9316335, Norton, 46 $m^2/g$, largely monoclinic) with $Pt(NO_3)_2$ and $Sn(OAc)_2$. The Pt content was 1% by weight, the Sn content was 0.5% by weight. The catalyst was calcined for 3 hours at 650° C.

Example 7

A catalyst was prepared by impregnation of a largely monoclinic $ZrO_2$ (support SN 9316321, Norton, 49 $m^2/g$) with a solution of 0.821 g of $Cr(NO_3)_3·9H_2O$ in 2.5 ml of water and subsequent impregnation with a solution of 1.763 g of $La(NO_3)_3$ in 2.5 ml of water. The catalyst was dried for 16 hours at 120° C. and calcined for 2 hours at 500° C. The finished catalyst had a chromium content of 0.9% and a lanthanum content of 4.5% by weight.

Comparative Experiments C1–C4

The comparative catalysts (C1: 10% $Cr/Al_2O_3$, C2: 1% $Cr/Al_2O_3$ and C3: 5% $Cr/Al_2O_3$) were prepared by impregnation of α-Al$_2$O$_3$ (9.5 m$^2$/g) with different amounts of Cr(NO$_3$)$_3$. These catalysts were dried for 6 hours at 120° C. and subsequently calcined for 2 hours at 500° C. The comparative catalyst C4 was prepared by impregnation of the same Al$_2$O$_3$ support with Pt(NO$_3$)$_2$. The catalyst was dried for 16 hours at 120° C. and subsequently calcined for 2 hours at 500° C.

Dehydrogenation

The dehydrogenation was carried out in a micro-fixed-bed pulse reactor at 500° C. For this purpose, about 0.6 g of the catalyst were weighed into a micro-fixed bed and a propane gas without the addition of hydrogen (without H$_2$) was passed through the catalyst in pulses, ie. with a regularly interrupted flow, at atmospheric pressure. The reaction products were analyzed quantitatively for each pulse by means of on-line GC. Between each pair of successive propane pulses (about 1.5 minutes apart), helium carrier gas flowed through the reactor.

A single pulse comprised about 100 μl of propane. The flow rate of the carrier gas was about 21.5 ml/min. The residence time was, depending on the bed height of the catalyst (from 10 to 25 mm), from about 1 to 2 seconds. The WHSV over the catalyst during a pulse was, likewise depending on the bed height, from 1.7 to 3.4. The results achieved are shown in Table 1 and are based on the maximum conversion achieved.

TABLE 1

Catalyst performance in the dehydrogenation of propane in a pulse reactor

| Example | Catalyst | Residence time [s] | Bed height | Y [%] | Conv. [%] | Sel. [%] |
|---|---|---|---|---|---|---|
| 1 | La/Cr/ZrO$_2$ | 0.8 | 15 mm | 50 | 54 | 92 |
| 2 | La/Cr/ZrO$_2$ | 0.8 | 15 mm | 49 | 53 | 92 |
| 3 | La/Cr/ZrO$_2$ | 0.8 | 15 mm | 47 | 51 | 92 |
| 4 | La/Cr/ZrO$_2$ | 0.8 | 15 mm | 49 | 53 | 92 |
| 5 | 1% Pt/0.5% Sn/ZrO$_2$ | 1.2 | 23 mm | 49 | 53 | 92 |
| 6 | 1% Pt/0.5% Sn/ZrO$_2$ | 1.2 | 23 mm | 43 | 44 | 97 |
| 7 | La/Cr/ZrO$_2$ | 1.3 | 24 mm | 35 | 36 | 96 |
| C1 | 10% Cr/Al$_2$O$_3$ | 1.3 | 25 mm | 25 | 26 | 96 |
| C2 | 1% Cr/Al$_2$O$_3$ | 1.3 | 24 mm | 14 | 18 | 79 |
| C3 | 5% Cr/Al$_2$O$_3$ | 1.2 | 23 mm | 22 | 23 | 95 |
| C4 | 1% Pt/Al$_2$O$_3$ | 1.3 | 24 mm | 5 | 59 | 9 |

It should be noted that the significantly higher conversion compared with the equilibrium position (500° C.) is achieved by the pulse operation in which, owing to the short residence time and the interval of about 1.5 min between the pulses, no thermodynamic equilibrium is established. Nevertheless, this method allows a good comparison of the selectivity at a high conversion.

The catalysts of the present invention enable, at the same temperature, higher conversions than with the comparative catalysts to be achieved at comparably high selectivity. The yields are therefore significantly higher for the catalysts of the present invention than for the comparative catalysts.

We claim:

1. A catalyst, for the preparation of olefinically unsaturated hydrocarbons from corresponding saturated hydrocarbons by dehydration, comprising a) zirconium oxide of which more than 90% is in the monoclinic modification, b) at least one element selected from the elements of the transition groups VIII and VI, c) rhenium and/or tin, and d) at least one compound selected from the compounds of the alkali metals, the alkaline earth metals, the elements of main group III, transition group III and zinc.

2. A catalyst as claimed in claim 1 comprising from 0.005 to 5% by weight of palladium, platinum, rhodium and/or rhenium.

3. A catalyst as claimed in claim 1 comprising a lanthanum, yttrium, gallium, indium or thallium compound as compounds of main group III or transition group III.

4. A catalyst as claimed in claim 1 comprising a chromium and/or tungsten compound as compound of transition group VI.

* * * * *